United States Patent
Gioia et al.

(10) Patent No.: US 9,045,720 B2
(45) Date of Patent: *Jun. 2, 2015

(54) HERBICIDAL COMPOSITION COMPRISING AN AMINOPHOSPHATE OR AMINOPHOSPHONATE SALT, A BETAINE AND AN AMINE OXIDE

(75) Inventors: Paul Gioia, Victoria (AU); Poay Huang Chuah, Singapore (SG); Wenbing Xie, Singapore (SG)

(73) Assignee: RHODIA CHIMIE, Aubervilliers (FR)

( * ) Notice: Subject to any disclaimer, the term of this patent is extended or adjusted under 35 U.S.C. 154(b) by 1456 days.

This patent is subject to a terminal disclaimer.

(21) Appl. No.: 11/794,299

(22) PCT Filed: Dec. 30, 2005

(86) PCT No.: PCT/EP2005/014146
§ 371 (c)(1),
(2), (4) Date: Oct. 25, 2007

(87) PCT Pub. No.: WO2006/069794
PCT Pub. Date: Jul. 6, 2006

(65) Prior Publication Data
US 2008/0103047 A1 May 1, 2008

Related U.S. Application Data

(60) Provisional application No. 60/640,300, filed on Dec. 30, 2004.

(51) Int. Cl.
*A01N 57/18* (2006.01)
*C11D 1/90* (2006.01)
*A01N 57/20* (2006.01)
*C11D 3/36* (2006.01)

(52) U.S. Cl.
CPC .... *C11D 1/90* (2013.01); *A01N 57/20* (2013.01); *C11D 3/364* (2013.01)

(58) Field of Classification Search
USPC ........................................ 504/206
See application file for complete search history.

(56) References Cited

U.S. PATENT DOCUMENTS

| | | | |
|---|---|---|---|
| 3,225,074 A | 12/1965 | Cowen et al. | |
| 3,527,593 A * | 9/1970 | Bland et al. | 504/244 |
| 3,723,357 A | 3/1973 | Hansen | |
| 3,882,051 A | 5/1975 | Hansen | |
| 4,011,388 A | 3/1977 | Murphy et al. | |
| 4,107,328 A | 8/1978 | Michaels | |
| 4,117,107 A | 9/1978 | Shapiro et al. | |
| 4,122,159 A | 10/1978 | Madrange et al. | |
| 4,137,191 A | 1/1979 | Lohr | |
| 4,243,549 A | 1/1981 | Messenger et al. | |
| 4,452,732 A | 6/1984 | Bolich, Jr. | |
| 4,477,365 A | 10/1984 | Verboom et al. | |
| 4,585,846 A | 4/1986 | Schulz et al. | |
| 4,607,076 A | 8/1986 | Schulz et al. | |
| 4,650,848 A | 3/1987 | Schulz et al. | |
| 4,703,797 A | 11/1987 | Djabbarah | |
| 4,708,998 A | 11/1987 | Schulz et al. | |
| 4,742,135 A | 5/1988 | Schulz et al. | |
| 4,788,247 A | 11/1988 | Schulz et al. | |
| 4,822,847 A | 4/1989 | Schulz et al. | |
| 4,831,092 A | 5/1989 | Bock et al. | |
| 4,835,234 A | 5/1989 | Valint et al. | |
| 4,882,405 A | 11/1989 | Schulz et al. | |
| 4,996,045 A | 2/1991 | Leighton et al. | |
| 5,153,289 A | 10/1992 | Schulz et al. | |
| 5,164,120 A | 11/1992 | Borland et al. | |
| 5,180,414 A | 1/1993 | Darchy et al. | |
| 5,258,358 A | 11/1993 | Kocur et al. | |
| 5,292,942 A | 3/1994 | Aigner et al. | |
| 5,338,793 A | 8/1994 | Loftin | |
| 5,341,932 A | 8/1994 | Chen et al. | |
| 5,354,906 A | 10/1994 | Weitmeyer et al. | |
| 5,385,206 A | 1/1995 | Thomas | |
| 5,439,317 A | 8/1995 | Bishop et al. | |
| 5,464,806 A | 11/1995 | Kassebaum et al. | |
| 5,551,516 A | 9/1996 | Norman et al. | |
| 5,580,856 A | 12/1996 | Prestrelski et al. | |
| 5,612,285 A | 3/1997 | Arnold | |
| 5,686,400 A | 11/1997 | Urfer et al. | |
| 5,700,760 A | 12/1997 | Magin et al. | |
| 5,703,016 A | 12/1997 | Magin et al. | |
| 5,747,416 A | 5/1998 | McArdle et al. | |
| 5,863,863 A | 1/1999 | Hasebe et al. | |

(Continued)

FOREIGN PATENT DOCUMENTS

| | | |
|---|---|---|
| CA | 2554335 | 8/2005 |
| EP | 0370338 | 5/1990 |

(Continued)

OTHER PUBLICATIONS

Ullmann's Encyclopedia of Industrial Chemistry, 5th Ed., vol. A 10, Edited by Gerhartz et al., pp. 176-177, Wiley-VCH Verlag GmbH & Co. KGaA, Weinheim, Germany, 1987.
"Application Guide for Household & Industrial Markets"; McIntyre Group Ltd., Copyright 2002, (Jan. 2003), obtained online @ http://www.dewolfchem.com/pdf/Mcintyre_HI&I_Application_Guide.pdf, (downloaded Mar. 6, 2012).
Surfactants by Albright & Wilson (Australia Limited ACN 004 234 137)—5 pp Feb. 1994.

(Continued)

*Primary Examiner* — Robert A Wax
*Assistant Examiner* — Thor Nielsen
(74) *Attorney, Agent, or Firm* — Dentons US LLP

(57) ABSTRACT

The present invention relates to herbicidal compositions comprising aminophosphate or aminophosphonate salts, particularly to herbicidal compositions comprising a high amount and aminophosphate or aminophosphonate salts and a betaine surfactant and an amine oxide surfactant.

22 Claims, No Drawings

(56) References Cited

U.S. PATENT DOCUMENTS

| | | | |
|---|---|---|---|
| 5,874,394 A | 2/1999 | Thomas et al. | |
| 5,888,934 A | 3/1999 | Townson et al. | |
| 5,897,699 A | 4/1999 | Chatterji et al. | |
| 5,912,209 A | 6/1999 | Kassebaum et al. | |
| 5,985,798 A | 11/1999 | Crudden | |
| 5,998,332 A | 12/1999 | Sato et al. | |
| 6,030,928 A | 2/2000 | Stahl et al. | |
| 6,036,638 A | 3/2000 | Nwawka | |
| 6,127,318 A | 10/2000 | Sato et al. | |
| 6,165,939 A | 12/2000 | Agbaje et al. | |
| 6,210,476 B1 | 4/2001 | Chatterji et al. | |
| 6,284,854 B1 | 9/2001 | Bowers et al. | |
| 6,288,010 B1 | 9/2001 | Rose et al. | |
| 6,302,209 B1 | 10/2001 | Thompson et al. | |
| 6,329,322 B1 | 12/2001 | Reierson | |
| 6,346,588 B1 | 2/2002 | Fench et al. | |
| 6,369,122 B1 | 4/2002 | Subramanyam | |
| 6,376,566 B1 | 4/2002 | Bergeron et al. | |
| 6,407,042 B1 | 6/2002 | Ward et al. | |
| 6,417,268 B1 | 7/2002 | Zhang et al. | |
| 6,432,878 B1 | 8/2002 | Brigance | |
| 6,432,884 B1 | 8/2002 | Lachut | |
| 6,451,731 B1 | 9/2002 | Agbaje et al. | |
| 6,500,784 B1 * | 12/2002 | Mille et al. | 504/206 |
| 6,566,408 B1 | 5/2003 | Cotrell et al. | |
| 6,642,178 B2 | 11/2003 | Woznica et al. | |
| 6,645,912 B1 * | 11/2003 | Mille et al. | 504/206 |
| 6,645,914 B1 | 11/2003 | Woznica et al. | |
| 6,653,257 B2 | 11/2003 | Mille et al. | |
| 6,770,268 B1 * | 8/2004 | Hall et al. | 424/54 |
| 6,770,594 B2 | 8/2004 | Bickers et al. | |
| 6,831,108 B2 | 12/2004 | Dahanayake et al. | |
| 6,881,707 B2 | 4/2005 | Howat et al. | |
| 6,992,046 B2 | 1/2006 | Bramati et al. | |
| 7,135,437 B2 | 11/2006 | Pallas et al. | |
| 7,316,990 B2 | 1/2008 | Tank et al. | |
| 8,236,730 B2 | 8/2012 | Bramati et al. | |
| 8,263,529 B2 | 9/2012 | Suzuki et al. | |
| 8,383,137 B2 | 2/2013 | Modaressi et al. | |
| 2002/0187917 A1 | 12/2002 | Lazarowitz | |
| 2003/0118540 A1 | 6/2003 | Charlton et al. | |
| 2004/0097372 A1 | 5/2004 | Abraham et al. | |
| 2004/0110644 A1 | 6/2004 | Halliday et al. | |
| 2004/0121917 A1 | 6/2004 | Pakulski | |
| 2005/0003965 A1 | 1/2005 | Xiao et al. | |
| 2005/0010009 A1 | 1/2005 | Schulz et al. | |
| 2005/0020454 A1 | 1/2005 | Francini et al. | |
| 2005/0130842 A1 | 6/2005 | Fleute-Schlachter | |
| 2005/0170965 A1 | 8/2005 | Bramati et al. | |
| 2006/0019830 A1 | 1/2006 | Xu et al. | |
| 2006/0060354 A1 | 3/2006 | Lewis et al. | |
| 2007/0155628 A1 | 7/2007 | Pazhianur et al. | |
| 2007/0282075 A1 | 12/2007 | Koch et al. | |
| 2008/0312083 A1 | 12/2008 | Gioia et al. | |
| 2009/0018018 A1 | 1/2009 | Gioia et al. | |
| 2010/0069269 A1 | 3/2010 | Prat et al. | |
| 2010/0093874 A1 | 4/2010 | Monin et al. | |
| 2010/0140531 A1 | 6/2010 | Prat et al. | |
| 2011/0009269 A1 | 1/2011 | Gioia et al. | |
| 2011/0015071 A1 | 1/2011 | Kisenwether et al. | |
| 2012/0040833 A1 | 2/2012 | Kisenwether et al. | |
| 2012/0165195 A1 | 6/2012 | Iskandar et al. | |

FOREIGN PATENT DOCUMENTS

| | | |
|---|---|---|
| EP | 0373851 | 6/1990 |
| EP | 0 274 369 B1 | 9/1990 |
| EP | 0449159 | 10/1991 |
| EP | 0483095 | 4/1992 |
| EP | 0508022 | 10/1992 |
| EP | 0573118 | 12/1993 |
| EP | 0810239 | 12/1997 |
| JP | 10183176 | 7/1998 |
| JP | 11-349826 | 12/1999 |
| WO | 9212637 | 8/1992 |
| WO | 92/14907 | 9/1992 |
| WO | 9701281 | 1/1997 |
| WO | 9706230 | 2/1997 |
| WO | 97/36489 | 10/1997 |
| WO | 98/14060 | 4/1998 |
| WO | 99/03895 | 1/1999 |
| WO | 99/15610 | 4/1999 |
| WO | WO 99/27048 A1 | 6/1999 |
| WO | 9945780 | 9/1999 |
| WO | 99/62338 | 12/1999 |
| WO | WO 00/38523 A1 | 7/2000 |
| WO | 0067571 | 11/2000 |
| WO | 0067573 | 11/2000 |
| WO | WO 01/08482 A1 | 2/2001 |
| WO | 0117358 | 3/2001 |
| WO | 0126463 | 4/2001 |
| WO | 0126469 | 4/2001 |
| WO | 0189302 | 11/2001 |
| WO | 02/26036 | 4/2002 |
| WO | 03/049813 | 6/2003 |
| WO | 2004/107861 | 12/2004 |
| WO | 2004107862 | 12/2004 |
| WO | 2007003112 | 1/2007 |

OTHER PUBLICATIONS

Empigen BB-AU alkyl betaine by Albright & Wilson Australia Limited (Incorporated in Victoria) Product Handling & Safety Bulletin—4 pp, 1983.

Basheva et al.; Role of Betaine as Foam Booster in the Presence of Silicone Oil Drops; Langmuir 2000, 16, 1000-1013; Received Jun. 16, 1999; 2000 American Chemical Society Published on Web Dec. 8, 1999.

* cited by examiner

HERBICIDAL COMPOSITION COMPRISING AN AMINOPHOSPHATE OR AMINOPHOSPHONATE SALT, A BETAINE AND AN AMINE OXIDE

CROSS REFERENCE TO PRIORITY APPLICATIONS

This application is the U.S. national phase of International Application No. PCT/EP2005/014146, filed Dec. 30, 2005, published in French as International Publication No. WO 2006/069794 A2 on Jul. 6, 2006, and claims priority of U.S. Application No. 60/640,300, filed Dec. 30, 2004, each hereby expressly incorporated by reference in its entirety and each assigned to the assignee hereof.

BACKGROUND OF THEN INVENTION

The present invention relates to herbicidal compositions comprising aminophosphate or aminophosphonate salts, particularly to herbicidal compositions comprising a high amount and aminophosphate or aminophosphonate salts and a betaine surfactant and an amine oxide surfactant.

Among various presentations of compositions comprising glyphosate, concentrated liquid compositions that can be diluted by the end-user (typically a farmer) are of interest. Usually, the higher the glyphosate concentration is, the better it is, because the end-user can set the use concentration (the amount of active applied to the field) by adjusting the dilution rate, and can avoid handling much product (for example the higher the concentration is, the lower the weight is).

Concentrated compositions can comprise a high amount of glyphosate, water, and at least one surfactant compound that can be useful as a formulation aid (dispersion, dissolution and/or stability of the glyphosate in water), and/or as a biological activator (for example increasing the efficacy of glyphosate salt, for example by encouraging wetting of a weed to be eliminated, or by encouraging penetration of the glyphosate into the weed). The amount of glyphosate, the nature of surfactant(s), the amount thereof, and possible further ingredients might have also an effect onto the rheological properties of the composition (for example viscosity, or ability to be spread), as such, or upon dilution. The rheological properties of the composition as such or upon dilution are important for handling and spreading purpose.

Where the concentration of glyphosate is high, crystallization is to be avoided. Crystallization can occur at different temperatures, at different glyphosate concentrations, or when diluting with water. The crystallization is characterized by formation of small solid particles comprising glyphosate. These small particles can have the bad impact of filters clogging, nozzles clogging, creating unnecessary hazardous waste problems to dispose off the crystals, loss of activity (bioefficacy), and/or bad repartition of the active on the field.

Compositions comprising glyphosate and ethoxylated fatty amines surfactants are known. However these compounds are believed to be rather ecotoxic, irritant or slightly biodegradable. There is a need for replacing these compounds or for reducing the amount thereof in the compositions.

Document WO 01/17358 (Monsanto) describes compositions comprising a high amount glyphosate isopropylamine salt and a mixture of surfactants comprising a surfactant of formula R—CO—NR'—(CR'$_2$)$_n$—COOM. The mixture of surfactants is taught enhancing herbicidal effectiveness. The surfactant is however expensive and there is a need for other solutions.

Document WO 03/063589 (Rhodia) describes compositions comprising 360 g/L of glyphosate isopropylamine salt (as glyphosate acid equivalent, 783 g/L as salt concentration), a betaine surfactant, and at least one further compound such as optionally ethoxylated amines or etheramines. There is a need for other solutions, especially for composition that are considered as less ecotoxic, and/or less sensitizing, and/or for composition that have improved bioefficacy.

There is a constant need for new compositions comprising an aminophosphate or aminophosphonate salt, especially a glyphosate salt, that can allow:

a low cost, especially low surfactant cost, and/or
an improved bioefficacy on at least some significant weeds, and/or
a good compatibility with other herbicides, pesticides, fertilizers, and/or fungicides associated by end-user for example to address some weed resistances, and/or
a good (low) sensitizing profile, and/or
a good ecotoxic profile, or an ecotoxic profile considered as good, and/or
high loads of aminophosphate or aminophosphonate salt that simplify handling and transportation, and/or
a good stability, typically without crystals formation, and/or
a compromise of the above.

BRIEF SUMMARY OF THE INVENTION

The invention addresses at least one of the needs or concerns above. Thus the invention relates to a herbicidal composition comprising:

optionally water,
an aminophosphate or aminophosphonate salt, preferably a glyphosate or guphosinate salt,
a surfactant system comprising:
  optionally water
  a betaine surfactant being:
    a betaine having formula $R^1R^2R^2N^+$—$CH_2COO.^-$ (I),
    a betaine having formula $R^1$—CO—NH—$R^4$—$R^2R^2N^+$—$CH_2COO^-$ (II), or
    a mixture or association thereof,
  an amine oxide surfactant being:
    an amine oxide having formula $R^1R^2R^2N{\rightarrow}O$ (III),
    an amine oxide having formula $R^1$—CO—NH—R4-$R^2R^2N{\rightarrow}O$ (IV), or
    a mixture or association thereof,
  wherein:
  $R^1$ which is identical or different, is a linear or branched hydrocarbon group, preferably an alkyl group containing 3 to 30 carbon atoms, preferably 3 to 20 carbon atoms,
  $R^2$, which is identical or different, is a $C_1$-$C_3$ alkyl group, preferably a methyl group,
  $R^4$, which is identical or different, is divalent linear or branched hydrocarbon group containing 1 to 6 carbon atoms, optionally substituted with a hydroxyl group, preferably a group of formula —$CH_2$—$CH_2$—$CH_2$— or —$CH_2$—CHOH—$CH_2$—, and
  optionally at least one surfactant different from the surfactants of formula (I) to (IV).

The composition is preferably a liquid aqueous herbicidal composition, comprising water.

According to another aspect the invention relates to a process for preparing the composition.

According to another aspect the invention relates to the use of a surfactant system comprising the betaine surfactant and the amine oxide surfactant in a herbicidal composition comprising the aminophosphate or aminophosphonate salt.

According to another aspect the invention relates to a surfactant blend comprising:
water, and
at least 10% by weight, preferably at least 15%, preferably at least 20%, preferably at least 25%, of a surfactant mixture comprising:
   a betaine surfactant being:
      a betaine having formula $R^1R^2R^2N^+$—$CH_2COO^-$ (I),
      a betaine having formula $R^1$—CO—NH—$R^4$—$R^2R^2N^+$—$CH_2COO^-$ (II), or
      a mixture or association thereof,
   an amine oxide surfactant being:
      an amine oxide having formula $R^1R^2R^2N{\rightarrow}O$ (III),
      an amine oxide having formula $R^1$—CO—NH—$R^4$—$R^2R^2N{\rightarrow}O$ (IV), or
      a mixture or association thereof,
   wherein:
      $R^1$ which is identical or different, is a linear or branched hydrocarbon group, preferably an alkyl group containing 3 to 30 carbon atoms, preferably 3 to 20 carbon atoms,
      $R^2$, which is identical or different, is a $C_1$-$C_3$ alkyl group, preferably a methyl group,
      $R^4$, which is identical or different, is divalent linear or branched hydrocarbon group containing 1 to 6 carbon atoms, optionally substituted with a hydroxyl group, preferably a group of formula —$CH_2$—$CH_2$—$CH_2$— or —$CH_2$—CHOH—$CH_2$—,
      the weight ratio between the betaine surfactant and the amine oxide surfactant is of from 10/90 to 90/10.

The surfactant blend thus provides an especially useful ingredient for the herbicidal composition.

According to another aspect the invention relates to the use of the surfactant blend, as a part of or as the whole surfactant system, in a herbicidal composition comprising the aminophosphate or aminophosphonate salt.

The invention also relates to the use of the composition.

DETAILED DESCRIPTION OF THE INVENTION

Definitions

In the present specification, unless otherwise provided, the amounts of aminophosphate or aminophosphonate salt, preferably a glyphosate or gluphosinate salt, are expressed as acid equivalents.

In the present specification, unless otherwise provided, the amounts of surfactant system or ingredients being used (such as betaine surfactant composition of matter, amine oxide surfactant composition of matter, surfactant blend), are the amounts "as is". These are the total amounts of a mixture or association, as opposed to amounts as active matter, dry matter amounts (solid content), or the like.

In the present specification, unless otherwise provided, the amounts of surfactant active matter (or "active surfactant matter"), for a surfactant ingredient or system (such as betaine surfactant composition of matter, amine oxide surfactant composition of matter, surfactant blend), are defined as the dry matter amount of the surfactant ingredient or system, minus the total amount of salt in the surfactant ingredient or system.

In the present specification, "chloride based salts" refer to any salt having $Cl^-$, particularly KCl or NaCl. The amounts thereof can be determined by conventional means. The amounts, unless otherwise provided, relate to amounts by weight in the herbicidal composition.

In the present specification, "substantially no sodium cation" refers to amounts of sodium cations of lower than 1% by weight, preferably lower than 0.1%, preferably lower than 0.01%.

In the present specification, a "surfactant system" refers to an association or mixture of surfactants which are provided separately in the composition or as a mixture prepared before introduction. The mixture can be for example a surfactant blend.

In the present specification the "surfactant blend" refers to a composition of matter comprising water, the betaine surfactant and the amine oxide surfactant. It does not comprise the aminophosphate or aminophosphonate salt. It is possible that the blend comprise at least one different surfactant, but it is not preferred. In the present specification a "blend adduct" refers to a surfactant blend obtained by preparing the betaine surfactant and the amine oxide surfactant in the same course of process, typically in a single reactor (batch). In the present specification a "blend mix" refers to a surfactant blend obtained by mixing a betaine surfactant (typically a betaine surfactant composition of matter) and an amine oxide surfactant (typically an amine oxide surfactant composition of matter) both prepared previously separately.

Surfactants are usually reaction adducts comprising several different compounds. These different compounds can have effects on the herbicidal composition. Hence it is referred to surfactant compositions of matter, and to surfactant blend if several surfactants (usually surfactant compositions of matter) are mixed. Thus in the present specification a betaine surfactant composition of matter is understood as a mixture comprising water, optionally a chlorine based salt, the betaine surfactant active molecule(s), and optionally further compounds such as pH buffers. In the present specification an amine oxide surfactant composition of matter is understood as a mixture comprising water, optionally a chlorine based salt, the amine oxide surfactant active molecule(s), and optionally further compounds such as pH buffers.

The ingredients of the composition are described below. Any combination thereof and therein can be implemented to defined, and/or prepare the composition according to the invention, and/or to use according to the invention.

Aminophosphate or Aminophosphonate Salt

Aminophosphate or aminophosphonate salts are known by the one skilled in the art.
Preferred salts are glyphosate or gluphosinate salts.
Glyphosate refers to N-(phosphonomethyl)glycine.
Gluphosinate refers to 4-[hydroxy(methyl)phosphinoyl]-DL-homoalanine.
The salts include:
sodium (Na) salts;
potassium (K) salts;
ammonium salts having $N(R)_4^+$ cations wherein R groups, identical or different, represent a hydrogen atom or a linear or non linear, saturated or unsaturated $C_1$-$C_6$ hydrocarbon group optionally substituted by a hydroxyl group, for example isopropylamine salts;
sulphonium salts; said salts being present alone or in a combination.

Ammonium salts that can in particular be cited include salts obtained from secondary or primary amines such as isopropylamine (IPA), dimethylamine, diamines such as ethylenediamine, or alkanolamines such as monoethanolamine (MEA). Trimethylsulphonium is a perfectly suitable sulphonium salt. Another suitable ammonium salt is the $NH_3$ salt (ammonium salt).

Preferred glyphosate salts for herbicidal application that can be cited are glyphosate potassium (K) salt, glyphosate sodium (Na) salt isopropylamine (IPA) salt, monoethanolamine (MEA) salt, trimethylsulphonium salt, potassium salt, ammonium ($NH_3$) salt, and mixtures or associations thereof, for example as taught in documents WO01/26469 (Nufarm) and WO03/013241 (Nufarm).

In the present invention isopropylamine containing salts are preferred. Thus in a preferred embodiment the salt is a glyphosate isopropylamine salt. In a preferred embodiment, the ratio between the cation such as the cation of isopropylamine and glyphosate is of about 1/1. However the ratio can of higher than 1/1. Such a ratio provides compositions having higher pH. The higher the pH, the lower the crystallization. pH can be also managed by using any other basic compound, for example KOH or other buffers.

Surfactant System

The surfactant system comprises the betaine surfactant, the amine oxide surfactant, optionally at least one surfactant different from the betaine and the amine oxide. The different surfactant(s) can be provided in the herbicidal composition as a separate ingredient; it can be thus referred to an association. In another embodiment, at least one of the different surfactant(s) can be provided as a mixture with the betaine surfactant and/or with the amine oxide surfactant and/or surfactant blend, it can be thus referred to a mixture or a blend. In that embodiment the different surfactant can be prepared separately and simply mixed with the betaine surfactant and/or amine oxide surfactant and/or surfactant blend. The different surfactant can also be prepared in the same course of process of the preparation of the betaine surfactant and/or amine oxide and/or surfactant blend, typically the blend adduct. Some useful different surfactant(s) are described below as further ingredients and as further surfactants.

Amine Oxide Surfactant

The amine oxide surfactant is:
an amine oxide of formula (III),
an amine oxide of formula (IV), or
a mixture thereof.

The amine oxide has preferably $R^2$ being a methyl group.
$R^1$ is preferably an alkyl group. This group is usually actually a mixture of different groups having different numbers of carbon atoms, being linear or branched, and optionally having some insaturations. These mixtures come from the reagents used to prepare them, which are actually distillation cuts and/or have a natural origin. In the present specification the number of carbon atoms in the $R^1$ group refers to the number of carbon atoms of the two most represented species.
Preferably:
$R^2$ is a methyl group, and
$R^1$ is a lauryl alkyl group mixture, preferably having more than 50% by weight of $C_{12}$ and,
$R^4$ if present is —$CH_2$—$CH_2$—$CH_2$—.

Amine oxides of formula (III) are preferred. They are often referred to as alkyl amine oxides, and are preferably an alkyldimethyl amine oxide based surfactant, for example lauryl dimethyl amine oxide based surfactant ($R^2$ is a methyl group, $R^1$ is a lauryl $C_{12}$ group). Amine oxides of formula (IV) are often referred to as alkyl amidoalkyl amine oxides.

Such surfactants are known by the one skilled in the art and are commercially available. Processes for preparing amine oxide surfactants are known by the one skilled in the art. Processes usually involve reacting an amine of formula $R^1NR^2R^2$ and/or $R^1$—CO—NH—$R^4$—$NR^2R^2$ with an oxidizing agent such as hydrogen peroxide $H_2O_2$, optionally in the presence of a complexant such as EDTA, and optionally regulating pH with a base such as NaOH or KOH. In the present invention the amine oxide surfactant is in an amine oxide surfactant composition of matter that preferably comprises substantially no sodium cation.

The amine oxide can be provided as an amine oxide surfactant composition of matter comprising water, the amine oxide and optionally a salt such as a potassium (preferred) or sodium based salt of chloride or hydroxide (preferred). The amine oxide surfactant composition of matter can typically comprise at least 25%, preferably at least 30%, by weight as active surfactant matter of the amine oxide, and preferably substantially no betaine (lower than 1% by weight as active matter, preferably lower than 0.1%, or even less, to none). The amine oxide surfactant composition of matter can also be a desalted surfactant composition of matter, comprising substantially no salt (lower than 1% by weight, preferably lower than 0.1%, or even less, to none). Processes for desalting surfactants are known by the one skilled in the art and are for example taught in document WO 00/38523.

Betaine Surfactant

The betaine surfactant is:
a betaine of formula (I),
a betaine of formula (II), or
a mixture thereof.
Preferably:
$R^2$ is a methyl group, and
$R^1$ is a lauryl alkyl group mixture, preferably having more than 50% by weight of $C_{12}$ and,
$R^4$ if present is —$CH_2$—$CH_2$—$CH_2$—.

The betaine has preferably $R^2$ being a methyl group.
$R^1$ is preferably an alkyl group. This group is usually actually a mixture of different groups having different numbers of carbon atoms, being linear or branched, and optionally having some insaturations. These mixtures come from the reagents used to prepare them, which are actually distillation cuts and/or have a natural origin. In the present specification the number of carbon atoms in the $R^1$ group refers to the number of carbon atoms of the two most represented species.

Betaines of formula (I) are preferred. They are often referred to as alkyl betaines, and are preferably an alkyldimethyl betaine based surfactant, for example lauryl dimethyl betaine based surfactant ($R^2$ is a methyl group, $R^1$ is a lauryl $C_{12}$ group). Betaines of formula (II) are often referred to as alkyl amidoalkyl betaines.

Such surfactants are known by the one skilled in the art and are commercially available. Processes for preparing betaine surfactants are known by the one skilled in the art. Processes usually involve reacting an amine of formula $R^1NR^2R^2$ and/or $R^1$—CO—NH—$R^4$—$NR^2R^2$ with monochloroacetic acid (MCA) or potassium (preferred) or sodium monochloroacetate (KMCA preferred or SMCA), and optionally regulating pH with a base such a NaOH or KOH (preferred). In the present invention the betaine is preferably in a betaine surfactant composition of matter that preferably comprises substantially no sodium cation.

The betaine can be provided as a betaine surfactant composition of matter comprising water, the betaine and optionally a salt such as potassium (preferred) or sodium based salt of chloride (preferred) or hydroxide. Preferably the betaine composition of matter is a potassium based surfactant composition of matter, for example obtained with using KMCA and/or KOH. The betaine surfactant composition of matter can typically comprise at least 25%, preferably at least 30%, by weight as active surfactant matter of the betaine, and preferably substantially no amine oxide (lower than 1% by weight as active matter, preferably lower than 0.1%, or even less, to none). The betaine surfactant composition of matter can also be a desalted surfactant composition of matter, comprising substantially no salt (lower than 1% by weight, preferably lower than 0.1%, or even less, to none). Processes for desalting surfactants include are known by the one skilled in the art and are for example taught in document WO 00/38523.

Betaine Surfactant Composition of Matter

The betaine surfactant composition of matter can advantageously comprise:
water,
a betaine having formula $R^1R^2R^2N^+$—$CH_2COO^-$, wherein $R^1$ and $R^2$ are as defined above:
at least 1% by weight of a chloride based salt, preferably of potassium chloride salt.

The betaine is a main surfactant compound of the betaine surfactant composition of matter. It is preferably the main surfactant compound of the surfactant system or surfactant blend. It is also referred to as the main surfactant. By main surfactant compound it is meant that said surfactant compound represents the highest surfactant active matter compared to optional other surfactant(s). For example, in a mixture or association comprising 40 parts as active of surfactant 1, 30 parts as active of surfactant 2, and 30 parts as active of surfactant 3, surfactant 1 would be considered as main surfactant even if it represents lower than 50% of all surfactants.

Preferably the betaine active matter represents at least 30% by weight, preferably at least 50%, of the total surfactant active matter of the betaine surfactant composition of matter, preferably of the surfactant blend or system in the composition.

Advantageously the betaine surfactant composition of matter comprises:
water,
at least 25%, preferably at least 30%, by weight as active surfactant matter of the betaine,
at least 2%, preferably at least 5%, by weight of a potassium chloride salt.

Preferably the betaine surfactant composition of matter comprises:
water,
at least 30%, preferably at least 35% by weight as active surfactant matter of the betaine,
at least 5% by weight of a potassium chloride salt, and substantially no sodium cation.

The betaine surfactant composition of matter can be obtained by, and is preferably obtained from, a process comprising the following steps:
step 1) reacting a compound of formula $R^1R^2R^2N$ with monochloroacetic acid, to obtain a reaction product;
step 2) adding potassium hydroxide to increase the pH,
step 3) optionally adding some further ingredients or adjusting the concentration or pH.

It is mentioned that step 1 and step 2 can also be performed simultaneously, by adding potassium hydroxide during reaction completion or by adding progressively chloroacetic acid and potassium hydroxide.

In another embodiment potassium chloroacetate is used in step 1) instead of chloroacetic acid, and step 2) is optional.

In a preferred embodiment, the process does not comprise any desalination step or ion exchange step. Thus the process is cost effective, and therefore the herbicidal composition can also be cost interesting.

Betaine and Amine Oxide Associations and/or Surfactant Blends

Compositions comprising an association in the surfactant system, for example as a surfactant blend, of a betaine of formula (I) and of an amine oxide of formula (III) are preferred.

Advantageously:
the betaine surfactant composition of matter comprises:
water,
at least 25%, preferably at least 30%, by weight as active surfactant matter of the betaine,
at least 2%, preferably at least 5%, by weight of a potassium chloride salt,
preferably substantially no sodium cation, and/or
the amine oxide surfactant composition of matter comprises:
water,
at least 25%, preferably at least 30%, by weight as active surfactant matter of the amine oxide, or
the surfactant blend comprises:
water,
at least 20%, preferably at least 25%, preferably at least 30%, by weight as active surfactant matter of the betaine together with the amine oxide
optionally at least 1% by weight, preferably at least 2%, preferably at least 3%, of a potassium salt, preferably of a potassium chloride salt,
preferably substantially no sodium cation.

Preferably the weight ratio between the betaine surfactant and the amine oxide surfactant as per active surfactant matter is of from 30/70 to 70/30, preferably from 50/50 to 70/30. This ratio can be applied to the composition, to the surfactant system, or to the surfactant blend In one embodiment the betaine surfactant is provided as a betaine surfactant composition of matter comprising the betaine(s) and water, separately from the amine oxide surfactant, the amine oxide being optionally provided as an amine oxide surfactant composition of matter.

In another embodiment the betaine surfactant and the amide oxide surfactant are provided as a surfactant blend, comprising the betaine(s), the amine oxide(s), and water. The surfactant blend can be a blend adduct or a blend mix. The blend mix can be typically obtained by mixing a betaine surfactant composition of matter, preferably a potassium based one or a desalted one, and an amine oxide surfactant composition of matter.

The surfactant blend is preferably a potassium based blend, for example obtained from a potassium based betaine surfactant composition of matter, or obtained as a blend adduct from a preparation involving using KMCA and/or KOH, and preferably comprising substantially no sodium cation and/or obtained with using substantially no SMCA and/or NaOH. The surfactant blend can also be a desalted surfactant blend comprising substantially no salt (lower than 1% by weight, preferably lower than 0.1%, or even less, to none), for example obtained by mixing desalted or substantially salt-free surfactant compositions of matters, and by mixing surfactant compositions of matter then desalting. Processes for desalting surfactants are known by the one skilled in the art and are for example taught in document WO 00/38523.

Advantageously the surfactant blend comprises at least 1% by weight, preferably at least 2%, preferably at least 3%, of a potassium salt, preferably of potassium chloride salt.

Advantageously the surfactant blend comprises at least 20%, preferably at least 25%, preferably at least 30%, by weight as active surfactant matter of the betaine together with the amine oxide, and at least 2% by weight of potassium chloride, and preferably substantially no sodium cation.

As explained above the surfactant blend can be prepared by a mixture route. Alternatively the surfactant blend can be obtained as a blend adduct in the same course of process by preparing first the betaine then the amine oxide in the same reactor from an amine of formula $R^1NR^2R^2$ and/or $R^1$—CO—NH—$R^4$—$NR^2R^2$, or by preparing first the amine oxide then the betaine in the same reactor from an amine of formula $R^1NR^2R^2$ and/or $R^1$—CO—NH—$R^4$—$NR^2R^2$, or by preparing simultaneously the amine oxide and the betaine in the same reactor from an amine of formula $R^1NR^2R^2$ and/or $R^1$—CO—NH—$R^4$—$NR^2R^2$. In these processes it is possible to load an excess of the amine for a part of it to be reacted during first stage, and the remaining to be reacted during the second stage. It is also possible to load some amine for the first stage and some amine for the second stage, with optionally changing the amine at each step. Each stage can be substantially carried out as described above for individual betaine surfactant and amine surfactant.

The ratios between the betaine and the amine oxide can be controlled by controlling the amounts of reagents.

A particularly interesting process for preparing a surfactant blend comprises the steps of:
  step 1) reacting an excess of a compound of formula $R^1NR^2R^2$ and/or $R^1$—CO—NH—$R^4$—$NR^2R^2$ with monochloroacetic acid or a salt thereof, optionally with a hydroxide salt being present, to obtain a reaction product comprising unreacted compound of formula $R^1NR^2R^2$ and/or $R^1$—CO—NH—$R^4$—$NR^2R^2$ and a betaine of formula (I) and/or (II),
  step 2) further reacting unreacted compound of formula $R^1NR^2R^2$ and/or $R^1$—CO—NH—$R^4$—$NR^2R^2$ with an oxidizing agent, preferably with hydrogen peroxide,
  step 3) optionally adding some further ingredients or adjusting the concentration or pH, or
  step 1') reacting an excess of a compound of formula $R^1NR^2R^2$ and/or $R^1$—CO—NH—$R^4$—$NR^2R^2$ with an oxidizing agent, preferably with hydrogen peroxide, to obtain a reaction product comprising unreacted compound of formula $R^1NR^2R^2$ and/or $R^1$—CO—NH—$R^4$—$NR^2R^2$ and an amine oxide of formula (III) and/or (VI),
  step 2') further reacting unreacted compound of formula $R^1NR^2R^2$ and/or $R^1$—CO—NH—$R^4$—$NR^2R^2$ with monochloroacetic acid or a salt thereof, optionally with a hydroxide salt being present,
  step 3') optionally adding some further ingredients or adjusting the concentration or pH.

Preferably in steps 1) or 2'), monochloroacetic acid (MCA) and KOH (preferred) or NaOH can be used, with introducing MCA first and then introducing progressively or at end of reaction KOH (preferred) or NaOH. Alternatively KMCA (preferred) or SMCA can be used, with further optionally KOH (preferred) or NaOH being introduced progressively at the end of the reaction.

Advantageously:
in step 1) monochloroacetic acid with potassium hydroxide is used, at a pH of from 7.5 to 9.5, at a temperature of from 80° C. to 100° C.,
in step 2) hydrogen peroxide is added progressively, at a temperature of from 60 to 80° C.

pH can be adjusted with a potassium based compound such as KOH or any other compound.

pH of the surfactant blend is preferably of from 7 to 9, as is.

Further Ingredients

The herbicidal composition can comprise further ingredients, such as:
surfactants different from the betaine of the betaine and amine oxide, as part of the surfactant system,
anti-foaming agents,
solvents, preferably water miscible solvent, preferably polar solvents, or
deposition control agents such as anti-rebound or anti-drift agents, optionally added afterward.

The one skilled in the art knows further ingredients that can be used for managing some properties or features of the composition and/or for adding benefits.

The formulations can for example comprise for example:
organopolysiloxanes antifoaming agent;
thickening agents such as xanthan gum type polysaccharides, alginates, carboxylated or hydroxylated methylcelluloses, synthetic macromolecules of the polyacrylate, polymaleate, polyvinylpyrrolidone, polyethylene glycol or polyvinyl alcohol type, or of the inorganic type such as bentonites.
auxiliary additives such as antioxidants, anti-UV agents, colorants, etc.
solvent such as an alcohol, for example isopropanol, typically up to 15% by weight.

The amount of these additives listed above is normally less than 10% by weight, preferably 1% by weight or less, advantageously 0.1% by weight or less compared with the composition weight.

Other Surfactants

The herbicidal composition can comprise a further surfactant, different from the betaine of the betaine surfactant composition matter. This further surfactant can provide further advantages or synergies in term of costs, and/or bioefficacy, and/or rheology management, and/or environment concerns and/or sensitivity concerns.

Examples of further surfactants include:
an ethoxylated fatty amine, a fatty amine,
an ether carboxylate,
an acid or non acid mono- and di-ester phosphate, optionally polyalkoxylated,
an alkylmonoglycoside or alkylpolyglycoside, advantageously octylglycoside, an octylpolyclycoside, decylglycoside, a decylpolyglycoside, or a mixture thereof, or mixtures thereof.

The fatty amines or ethoxylated fatty amines can comprise at least one hydrocarbon group containing 2 to 24 carbon atoms, optionally polyalkoxylated.

The fatty amines or ethoxylated fatty amines can more particularly be selected from amines comprising at least one linear or branched, saturated or unsaturated group containing 2 to 24 carbon atoms, preferably 8 to 18 carbon atoms, optionally comprising 2 to 30 oxyethylene groups, or a mixture of a plurality thereof. Examples include ethoxylated tallow amines.

The fatty amines or ethoxylated fatty amines can be selected from ethoxylated fatty amines comprising at least one linear or branched, saturated or unsaturated groups containing 6 to 24 carbon atoms, preferably 8 to 20 carbon atoms, comprising 2 to 30 oxyethylene groups, or a mixture of a plurality thereof. Examples include the compounds having the following formula:

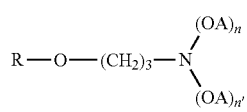

wherein R represents a linear or branched, saturated or unsaturated hydrocarbon group containing 6 to 24 carbon atoms, preferably 8 to 20 carbon atoms; OA represents an oxypropylene group; and n, n', which may or may not be identical, represent a mean number in the range 1 to 30.

Examples of such amines that can be cited are amines derived from copra and containing 5 oxyethylene (OE)

motifs, oleic amines containing 5 OE, amines derived from tallow containing 5-20 OE, for example 10, compounds corresponding to the above formula, in which R is an alkyl group containing 12 to 15 carbon atoms, the number of OE motifs being in the range 20 to 30.

The amount of fatty amines or ethoxylated fatty amines can be of from 0 (none) to 120 g/l of the composition, preferably of from 0 (none) to 60 g/l.

The ether carboxylate has preferably formula $R(OCH_2CH_2)_nOCH_2CO_2^-$, wherein R is a linear or branched alkyl, alkenyl, alkylphenyl or polypropyleneoxy group having from 6 to 20, for example 8 to 14, aliphatic carbon atoms and n is of from 1 to 30, preferably of from 2 to 20. The ether carboxylate has preferably a counter ion being ammonium or potassium, or obtained from an amine or alkanolamine having up to 6 carbon atoms.

The acid or non acid mono- and di-ester phosphate, optionally polyalkoxylated is selected from acid or non acid phosphate mono- or di-esters, optionally polyalkoxylated, with the formula below:

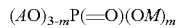

$$(AO)_{3-m}P(=O)(OM)_m$$

wherein:
A, identical or different, represents a group $R'^1$—O(CH$_2$—CHR'$^2$—O)$_n$ wherein:
  $R'^1$, identical or different, represents a linear or non linear, saturated or unsaturated $C_6$-$C_{20}$ hydrocarbon group, preferably $C_8$-$C_{18}$;
  $R'^2$, identical or different, represents a hydrogen atom or a methyl or ethyl group, preferably a hydrogen atom;
  n is a mean number of motifs in the range 0 to 10, preferably in the range 2 to 10;
M, identical or different, represents a hydrogen atom, an alkali or alkaline-earth metal, a $N(R^3)_4^+$ type radical wherein $R^3$, identical or different, represents a hydrogen atom or a linear or non linear, saturated or unsaturated $C_1$-$C_6$ hydrocarbon group optionally substituted with a hydroxyl group;
m is a whole or average number in the range 1 to 2.

The acid or non acid mono- and di-ester phosphate, optionally polyalkoxylated can be in the form of a monoester, a diester, or a mixture of these two esters.

The amount of acid or non acid mono- and di-ester phosphate, optionally polyalkoxylated can be of from 0 (none) to 120 g/l of the composition.

Process for Preparing the Herbicidal Composition

The composition of the invention can be prepared by mixing their different ingredient with moderate stirring.

This operation preferably takes place at a temperature in the range 15° C. to 60° C., preferably at a temperature close to ambient temperature (15-30° C.).

The surfactant system, for example the surfactant blend, is preferably only added once the other constituents have been mixed.

Thus the process can comprise the step of mixing the aminophosphate or aminophosphonate salt with the betaine surfactant and the amine oxide surfactant, and the optional different surfactant(s). The betaine surfactant and the amine oxide surfactant can be provide in any form, separately, preferably as a betaine surfactant composition of matter comprising water and as an amine oxide surfactant composition of matter comprising water. The can be also provided together as a surfactant blend comprising the betaine surfactant and the amine oxide surfactant and water. Hence a useful process for preparing the composition comprises:
Step a) preparing a surfactant blend as mentioned above
Step b) mixing with the other ingredients.

Herbicidal Composition Preferred Features

Advantageously the composition is an aqueous composition, and:
the amount of the aminophosphate or aminophosphonate salt is of at least 360 g/L,
the amount of surfactant, preferably of the betaine with the amine oxide, is of at least 24 g/L as per active surfactant matter of the surfactant system.

Advantageously the surfactant system is provided with comprising water, in an amount "as is" of at least 80 g/L, preferably of at least 100 g/L.

Advantageously the amount of surfactant as per active surfactant matter of the surfactant system is of at least 25% by weight of the surfactant system.

Advantageously the betaine with the amine oxide represents at least 30% by weight as per active surfactant matter, preferably at least 50%, of the total surfactant active matter of the surfactant system in the composition.

Advantageously the composition comprises at least 80 g/L as is, preferably at least 100 g/L:
of the betaine surfactant composition of matter with the amine oxide optionally provided as an amine oxide composition of matter, or
of the surfactant blend.

Thus the betaine with the amine oxide, provided as surfactant compositions of matter or as surfactant blend can represent all or a part of the surfactant system in the composition.

Advantageously the composition comprises:
an amount of inorganic salts, preferably of chloride-based salts, of higher than 8%, preferably higher than 10%, preferably higher than 12%, by weight of the amount of the betaine surfactant composition of matter, or
an amount of inorganic salts, preferably of chloride-based salts, of higher than 0.2%, preferably higher than 3%, preferably higher than 4%, by weight of the amount of the surfactant active matter.

Advantageously the composition comprises:
from 360 g/L to 560 g/L of the aminophosphate or aminophosphonate salt, preferably of glyphosate salt, and
from 80 g/L to 160 g/L of the surfactant system as is.

Some compositions can typically comprise:
from 400 to 500 g/L of a glyphosate salt, preferably of glyphosate isopropylamine salt, and
from 30 to 40.5 g/L as per active surfactant matter of the surfactant system, preferably of the betaine with the amine oxide.

Some other compositions can typically comprise:
from 500 to 560 g/L of a glyphosate salt, preferably of glyphosate isopropylamine salt, and
at least 36 g/L, preferably at least 40.5 g/L as per active surfactant matter of the surfactant system, preferably of the betaine with the amine oxide.

At high loads of glyphosate salt, especially with salts different from potassium salts, for example with glyphosate isopropylamine salt, the invention allows among other handling less composition (higher load), with a good stability (no crystals) with an interesting bioefficacy and/or ecotoxic profile. The composition can allow also good compatibility with other herbicides used for example to address some weed resistances.

At low loads of glyphosate salt, especially with salts different from potassium salts, for example with glyphosate isopropylamine salt, the invention allows among other a good stability (no crystal) with an interesting bioefficacy and/or ecotoxic profile.

Use of the Composition

The herbicidal composition of the invention can be thus used to treat plants, normally after diluting with water. The diluted composition can be applied onto a field by any appropriate mean.

The dilution, and the application onto the field, can be for example such that the amount of aminophosphate or aminophosphonate salt, preferably glyphosate salt, is of from 500 g acid equivalent/ha to 1500 g acid equivalent/ha, typically from 600 to 1200 g/ha.

Upon dilution the end-user can admix other herbicides, pesticides, fertilizers, fungicides. For example the end-user can combine the glyphosate salt with other herbicides to address some weed resistances to glyphosate. The composition according to the invention, especially with glyphosate salt different from potassium salt, for example with glyphosate isopropylamine salt, provides a good compatibility with other herbicides. The invention can allow high loads of glyphosate salts with good compatibility.

Some details or advantages of the invention will appear in the non-imitative examples below.

EXAMPLES

Example 1

Preparation of a Surfactant Blend Comprising a Betaine Surfactant of Formula (I) and an Amine Oxide Surfactant of Formula (III)

The following raw materials are used:

| Product | Amount as is (parts by weight) | Concentration (% by weight) | Effective amount (parts by weight) |
|---|---|---|---|
| Lauryldimethylamine ($R^1$ is $C_{12}$) | 32.4 | 100 | 32.4 |
| Monochloroacetic acid (MCA) | 6.76 | 100 | 6.76 |
| KOH solution in water | 8.94 | 42.5 | 3.80 |
| $H_2O_2$ solution in water | 9.47 | 30 | 2.84 |
| EDTA solution in water | 1 | 5 | 0.05 |
| Water | 41.79 | 100 | 41.79 |

Procedure:

Step 1: in a batch mix the water, lauryldimethyl amine and the MCA and add KOH upon formation of gel and/or to control pH in the range 7-9, at temperature of about 90° C., until a conversion ratio of MCA of about 99% is achieved.

Step 2: Cool the batch to about 70° C., add the EDTA solution, and slowly introduce the $H_2O_2$ solution and in a way to avoid excessive exotherm with holding the reaction at about 70° C. until amine residue and hydrogen is of about 1%.

The product obtained has the following characteristics:

| Compound | Wt % | Mole per 100 parts | Mw (g/mol) |
|---|---|---|---|
| Betaine | 18.0 | 0.065 | 279 |
| Amine oxide | 18.0 | 0.076 | 237 |
| KCl | 4.81 | 0.082 | 58.5 |
| Free amine | 1 | 0.005 | 221 |
| Potassium Monochoroacetic acid | ≤0.5 | ≤0.004 | 132.6 |

Example 2

Preparation of a Surfactant Blend Comprising a Betaine Surfactant of Formula (I) and an Amine Oxide Surfactant of Formula (III)

Example 1 is reproduced with varying the amounts of MCA and $H_2O_2$ reagents to obtain a product having the following characteristics:

| Compound | Example 2.1 | Example 2.2 |
|---|---|---|
| Betaine wt % | 16.4 | 20.4 |
| Amine oxide wt % | 16.4 | 13.6 |
| KCl wt % | 4.4 | 5.4 |
| Free amine wt % | 0.5 | 0.9 |

Example 3

Compositions Comprising Glyphosate

The following compositions are prepared:

| | Example | | | | | |
|---|---|---|---|---|---|---|
| | 3.1 | 3.2 | 3.3 | 3.4 | 3.5 | 3.6 |
| Glyphosate IPA (acid equivalent) | 450 g/L | 450 g/L | 450 g/L | 510 g/L | 510 g/L | 510 g/L |
| Blend of example 1 (as is) | 120 g/L | | | 140 g/L | | |
| Blend of example 2.1 (as is) | | 120 g/L | | | 140 g/L | |
| Blend of example 2.2 (as is) | | | 120 g/L | | | 140 g/L |
| De-ionized water | | | To volume | | | |

The following characteristics are measured/evaluated:

| Composition | Example 3.3 | Example 3.6 |
|---|---|---|
| Initial ($T_o$) at room temperature (25° C.) | clear, colorless, homogeneous, semi-viscous liquid, pH: neat 4.91 | clear, colorless, homogeneous, semi-viscous liquid, pH: neat 4.8 |
| After 2 weeks at 0° C. | Stable | Stable |
| After 2 weeks at 54° C. | Stable pH 4.93 | Stable pH 4.85 |
| After 4 weeks at room temperature | Stable pH 4.80 | Stable pH 4.82 |
| After 4 weeks at 30° C. | Stable pH 4.82 | Stable pH 4.81 |
| After 4 weeks at 40° C. | Stable pH 4.83 | Stable pH 4.80 |

-continued

| Composition | Example 3.3 | Example 3.6 |
|---|---|---|
| After 8 weeks at room temperature | Stable pH 4.81 | Stable pH 4.82 |
| After 8 weeks at 30° C. | Stable pH 4.82 | Stable pH 4.82 |
| After 8 weeks at 40° C. | Stable pH 4.84 | Stable pH 4.83 |
| After 12 weeks at room temperature | Stable pH 4.83 | Stable pH 4.81 |
| After 12 weeks at 30° C. | Stable pH 4.82 | Stable pH 4.82 |

This shows that the compositions according to the invention have a good physical stability without crystallization, at high loads of glyphosate IPA.

Example 4

Activity in Glass-House Trials

Activity tests are performed for the compositions of the invention and for comparative compositions:
Roundup® CT, marketed by Monsanto, believed to be a 450 g/L glyphosate IPA composition.
Roundup® PowerMAX, marketed by Monsanto, believed to be an about 540 g/L glyphosate potassium composition
Tests
The activities of the compositions are compared when applied (by spraying) to canola.
Application Rate: Formulations applied at 35, 70 & 140 g ai/ha.
Test species: Canola (*Brassica napus* var. rainbow)
Days to spray: Canola: 18
Days from spray to assessment: 14*
Materials and Methods:
Plant Propagation
Canola seeds (5/pot) are sown at 2 mm depth in 10 cm diameter pots filled with potting mix (AS 3743) that have been amended with macro and micronutrients to ensure optimal growth. One week after seedling emergence, seedlings are thinned for uniform size to one seedling per pot. Canola are grown in a temperature-controlled greenhouse (14° C.-25° C.) for 8 days then outdoors for 10 days prior to spray application. After the application of herbicides the pots are returned to the greenhouse until plants are assessed for fresh weight.
Herbicide Application
Herbicide formulations are applied using an enclosed laboratory track-sprayer fitted with three 110° flat fan nozzles (Teejet XR11001-VS) spaced at 50 cm intervals across the boom. The boom moves along a fixed track at 6 km h$^{-1}$, sprayed at a water volume of 64 L ha$^{-1}$ with a pressure of 200 kPa.
Assessment
Seedlings are harvested 14DAT by cutting foliage off at base immediately prior to weighing on an AND FX 300 electronic balance (range 0-300 g).
Statistical Analysis
Data is analysed using a factorial design with two factors, Formulation and Rate. 95% least significant differences (LSD) are calculated for the mean of each treatment. The lowest fresh weight (ie. greatest herbicidal effect) is denoted with alpha code "a" when significantly different to other treatments, which are coded "b", "c", "d" etc. with increasing fresh weight.

Environmental Conditions
Temperature within the greenhouse is recorded at 9 AM, 12 PM and 5 PM daily following application of herbicides.

| | Temperature ° C. | | |
|---|---|---|---|
| Date | 9 AM | 12 PM | 5 PM |
| Day 1 | 21 | 26 | 23 |
| Day 2 | | | |
| Day 3 | | | |
| Day 4 | 24 | 28 | 28 |
| Day 5 | 20 | 24 | 21 |
| Day 6 | 18 | 25 | 22 |
| Day 7 | 20 | 25 | 23 |
| Day 8 | 21 | 24 | 23 |
| Day 9 | | | |
| Day 10 | | | |
| Day 11 | 20 | 25 | 22 |
| Day 12 | 21 | 24 | 22 |
| Day 13 | 22 | 24 | 21 |
| Day 14 | 20 | 23 | 22 |
| Day 15 | 17 | 22 | 21 |

Results (Formulation×Rate)
Composition of example 3.3 is slightly more efficient than comparative composition Roundup® CT, but is considered as bioequivalent, at 70 & 140 g ai/ha. See table 1 below.

TABLE 1

FAOV Table & significant differences Fresh weight (g)
14DAT-Canola-450 g/L formulations

| | Rate (g ai/ha) | | | Formulation |
|---|---|---|---|---|
| | 35 | 70 | 140 | Mean |
| UTC | | 5.87 | | |
| Roundup CT | 1.72 b | 0.69 a | 0.55 a | 0.99 a |
| Exemple 3.3 | 1.56 b | 0.66 a | 0.42 a | 0.88 a |
| Rate Mean | 2.09 c | 0.77 b | 0.48 a | |

Composition of example 3.6 is more efficient than comparative composition Roundup® CT, and is considered as bioequivalent to comparative composition Roundup® PowerMAX. See table 2 below.

TABLE 2

FAOV Table & significant differences Fresh weight (g)
14DAT-Canola-510 & 540 g/L formulations

| | Rate (g ai/ha) | | | |
|---|---|---|---|---|
| | 35 | 70 | 140 | Formulation Mean |
| UTC | | 5.87 | | |
| Roundup PowerMAX | 1.18 bc | 0.46 a | 0.53 a | 0.72 a |
| Example 3.6 | 1.35 c | 0.68 a | 0.45 a | 0.83 ab |
| Rate Mean | 1.67 b | 0.65 a | 0.50 a | |

Composition of example 3.6 can show better compatibility with other herbicides than comparative composition Roundup PowerMAX.

The invention claimed is:
1. A herbicidal composition comprising:
(i) optionally water,
(ii) at least 360 g/L of an aminophosphonate salt, and
(iii) a surfactant system which comprises:
optionally, water a betaine surfactant comprising:
  a betaine having the formula $R^1R^2R^2N^+$—$CH_2COO^-$ (I), and
an amine oxide surfactant comprising:
  an amine oxide having the formula $R^1R^2R^2N \rightarrow O$ (III),
  wherein:
    the radicals $R^1$, which may be identical or different, are each a linear or branched hydrocarbon radical having 3 to 30 carbon atoms, and
    the radicals $R^2$, which may be identical or different, are each a $C_1$-$C_3$ alkyl radical,
optionally, at least one surfactant other than the surfactants of formulae (I) and (III),
wherein the weight ratio between the betaine surfactant and the amine oxide surfactant ranges from 30/70 to 70/30, and
wherein the amount of betaine surfactant and amino oxide surfactant is at least 24 g/L of the surfactant system.

2. The herbicidal composition as defined by claim 1, wherein the aminophosphonate salt comprises a glyphosate isopropylamine salt, a glyphosate potassium salt, a glyphosate ammonium salt, a glyphosate sodium salt, a glyphosate monoethanolamine salt, or a mixture thereof.

3. The herbicidal composition as defined by claim 1, wherein the herbicidal composition comprises an aqueous composition, and the amount of the aminophosphonate salt in the composition is at least 400 g/L.

4. The herbicidal composition as defined by claim 1, wherein the surfactant system comprising water, is in an amount of at least 80 g/L.

5. The herbicidal composition as defined by claim 1, wherein the amount of betaine surfactant and amine oxide surfactant is at least 25% by weight of the surfactant system.

6. The herbicidal composition as defined by claim 1, wherein the betaine surfactant and the amine oxide surfactant constitute at least 30% by weight of the surfactant system.

7. The herbicidal composition as defined by claim 1, wherein the betaine surfactant is provided as a betaine surfactant composition comprising the betaine and water, separately from the amine oxide surfactant wherein the amine oxide being optionally provided as an amine oxide surfactant composition; or wherein the betaine surfactant and the amide oxide surfactant are provided as a surfactant blend, comprising the betaine, the amine oxide, and water.

8. The herbicidal composition as defined by claim 7, wherein the betaine surfactant is provided as a betaine surfactant composition comprising a potassium based betaine surfactant composition, or as a desalted surfactant composition; or wherein the surfactant system comprises a potassium based blend or a desalted surfactant blend.

9. The herbicidal composition as defined by claim 7, wherein the herbicidal composition comprises at least 80 g/L of the betaine surfactant composition with the amine oxide optionally provided as an amine oxide surfactant composition; or wherein the herbicidal composition comprises at least 80 g/L of the surfactant blend.

10. The herbicidal composition as defined by claim 7, wherein the betaine surfactant composition comprises:
  water,
  at least 25% by weight of betaine,
  at least 2% by weight of a potassium chloride salt, and
  optionally, substantially no sodium cation,
and/or
the amine oxide surfactant composition comprises:
  water, and
  at least 25% by weight of amine oxide,
or
the surfactant blend comprises:
  water, and
  at least 20% by weight of betaine together with amine oxide.

11. The herbicidal composition as defined by claim 10, wherein the surfactant blend comprises at least 3% by weight of a potassium salt, and substantially no sodium cation.

12. The herbicidal composition as defined by claim 1, wherein the herbicidal composition comprises from 360 g/L to 560 g/L of the aminophosphonate salt, and from 80 g/L to 160 g/L of the surfactant system.

13. The herbicidal composition as defined by claim 1, wherein the herbicidal composition comprises from 400 to 500 g/L of a glyphosate salt, and from 30 to 40.5 g/L of betaine surfactant and amine oxide surfactant of the surfactant system.

14. The herbicidal composition as defined by claim 1, wherein the herbicidal composition comprises from 500 to 560 g/L of a glyphosate salt, and at least 36 g/L of betaine surfactant and amine oxide surfactant of the surfactant system.

15. The herbicidal composition as defined by claim 1, wherein $R^2$ is a methyl radical, and $R^1$ is a lauryl alkyl radical mixture in formulae (I) and (III).

16. The herbicidal composition as defined by claim 1, wherein the surfactant system comprises at least one surfactant other than the surfactants of formula (I) and (III) selected from the group consisting of:
  an ethoxylated fatty amine,
  an ether carboxylate,
  an acid or non acid mono- or di-ester phosphate, optionally polyalkoxylated,
  an alkylmonoglycoside or alkylpolyglycoside, or
  mixtures thereof.

17. The herbicidal composition as defined by claim 1, further comprising:
  an anti-foaming agent(s),
  a solvent, and/or
  a deposition control, anti-rebound or anti-drift agent, optionally added subsequently.

18. A process for formulating a herbicidal composition as defined by claim 1, comprising mixing the aminophosphonate salt with the betaine surfactant and the amine oxide surfactant.

19. The process as defined by claim 18, wherein the betaine surfactant and the amine oxide surfactant are provided separately, optionally as a betaine surfactant composition comprising water and as an amine oxide surfactant composition comprising water.

20. The process as defined by claim 18, wherein the betaine surfactant and the amine oxide surfactant are provided as a surfactant blend comprising the betaine surfactant and the amine oxide surfactant and water.

21. The herbicidal composition of claim 1, wherein the surfactant system further comprises a betaine surfactant having the formula $$R^1\text{—CO—NH—}R^4\text{—}R^2R^2N^+\text{—CH}_2COO^- \quad (II),$$

wherein:
  the radical $R^1$ is a linear or branched hydrocarbon radical having 3 to 30 carbon atoms, and
  the radicals $R^2$, which may be identical or different, are each a $C_1$-$C_3$ alkyl radical, and
  the radical $R^4$ is —$CH_2$—$CH_2$—$CH_2$ or $CH_2$—CHOH—$CH_2$—.

22. The herbicidal composition of claim 1, wherein the surfactant system further comprises an amine oxide surfactant having the formula $$R^1-CO-NH-R^4-R^2R^2N\rightarrow O \quad (IV),$$

wherein:
  the radical $R^1$ is a linear or branched hydrocarbon radical having 3 to 30 carbon atoms, and
  the radicals $R^2$, which may be identical or different, are each a $C_1$-$C_3$ alkyl radical, and
  the radical $R^4$ is $-CH_2-CH_2-CH_2$ or $CH_2-CHOH-CH_2-$.

* * * * *